(12) United States Patent
Kettler et al.

(10) Patent No.: US 9,417,187 B2
(45) Date of Patent: Aug. 16, 2016

(54) METHOD FOR DETERMINING THE SURFACE GLOSS OF A COLOUR STANDARD

(71) Applicant: AXALTA COATING SYSTEMS IP CO., LLC, Wilmington (DE)

(72) Inventors: Wilhelm Kettler, Wuppertal (DE); Peter Jelen, Wermelskirchen (DE); Oliver Korten, Remscheid (DE)

(73) Assignee: AXALTA COATING SYSTEMS IP CO., LLC, Wilmington, DE (US)

( * ) Notice: Subject to any disclaimer, the term of this patent is extended or adjusted under 35 U.S.C. 154(b) by 0 days.

(21) Appl. No.: 14/799,771

(22) Filed: Jul. 15, 2015

(65) Prior Publication Data
US 2016/0025629 A1    Jan. 28, 2016

Related U.S. Application Data

(63) Continuation of application No. 14/360,928, filed as application No. PCT/US2012/065133 on Nov. 14, 2012, now abandoned.

(60) Provisional application No. 61/563,872, filed on Nov. 28, 2011.

(51) Int. Cl.
*G01N 21/55*     (2014.01)
*G01N 21/57*     (2006.01)
(Continued)

(52) U.S. Cl.
CPC .............. *G01N 21/57* (2013.01); *G01J 3/0251* (2013.01); *G01J 3/504* (2013.01); *G01N 2201/065* (2013.01)

(58) Field of Classification Search
CPC .................................................... G01N 21/55
USPC .......................................... 356/445, 402, 303
See application file for complete search history.

(56) References Cited

U.S. PATENT DOCUMENTS 6,226,085 B1    5/2001  Weber 7,158,672 B2 *  1/2007  Johansson ............. G01J 3/0251
                                                           382/167
2004/0252883 A1 * 12/2004  Johansson ............. G01J 3/0251
                                                           382/162

FOREIGN PATENT DOCUMENTS

EP        1631802 B1    8/2006
JP        6221924       8/1994
(Continued)

OTHER PUBLICATIONS

ISA European Patent Office, International Search Report and Written Opinion for International Application No. PCT/US2012/065133, dated Mar. 7, 2013.
(Continued)

*Primary Examiner* — Roy M Punnoose
(74) *Attorney, Agent, or Firm* — Ingrassia Fisher & Lorenz, P.C.

(57) ABSTRACT

The invention relates to a method for determining the gloss of a colour standard comprising the following steps:

A) experimentally determining reflection spectra R(exp) of the colour standard, comprising a first reflection spectrum and a second reflection spectrum, with an integrating sphere colour measurement instrument, wherein said first reflection spectrum is obtained at (A1) d/8°—geometry with the specular component included, and said second reflection spectrum is obtained at (A2) d/8°—geometry with the specular component excluded, and B) converting reflection spectra data of the experimentally determined reflection spectra R(exp) of the colour standard to gloss values by:

B1) acquiring the difference reflection spectrum ΔR of the experimentally determined reflection spectrum R(exp) with the specular component included (A1) and the reflection spectrum R(exp) with the specular component excluded (A2), and B2) determining the gloss values corresponding to said difference reflection spectrum ΔR with the assistance of previously prepared calibration curves, representing the functional relationship between the difference reflection spectrum ΔR and the gloss values measured at one or more gloss angles.

15 Claims, 7 Drawing Sheets

(51) Int. Cl.
*G01J 3/50* (2006.01)
*G01J 3/02* (2006.01)

(56) References Cited

FOREIGN PATENT DOCUMENTS

| JP | 9222361 | 8/1997 |
| JP | 2004317131 | 11/2004 |
| JP | 2010243353 | 10/2010 |
| WO | 2006013320 A1 | 2/2006 |

OTHER PUBLICATIONS

ISA European Patent Office, International Preliminary Report on Patentability for International Application No. PCT/US2012/065133, dated Jun. 12, 2014.
USPTO, Notice of Allowance issued in U.S. Appl. No. 14/360,928, dated May 1, 2015.

* cited by examiner

METHOD FOR DETERMINING THE SURFACE GLOSS OF A COLOUR STANDARD

CROSS-REFERENCE TO RELATED APPLICATION

This is a continuation of U.S. application Ser. No. 14/360,928, filed May 27, 2014, which was a U.S. National-Stage entry under 35 U.S.C. §371 based on International Application No. PCT/US2012/065133, filed Nov. 14, 2012 which was published under PCT Article 21(2) and which claims priority to U.S. Provisional Application No. 61/563,872, filed Nov. 28, 2011, which are all hereby incorporated in their entirety by reference.

FIELD OF THE INVENTION

The invention relates to a method for determining the gloss of a colour standard. The method can be used in the paint industry or other paint related fields.

DESCRIPTION OF RELATED ART

In industrial colour applications a variety of instruments are utilised for the assessment of colour and gloss of surface coatings and corresponding differences between sample pairs. Wherever technically feasible, visual assessments are replaced by instrumental assessments, which hence have to be reliable on the one hand and in conformity with visual perception on the other. Modern colour management systems have to be capable of dealing with colour information of different sources and account for specific differences of distributed heterogeneous instrumental families and historical data.

A very special problem in this context is the instrumental characterisation of physical surface texture of coatings giving rise to surface gloss which may assume any value between highly glossy and perfectly matt samples. If this gloss measure would be unique and could be related to the matting agent amount of a colour formulation the efficiency of computer-aided recipe calculation could be improved considerably. The instrumental characterisation of surface gloss is not trivial, since different surface topologies may give rise to the same visual appearance of a coating, i.e., there is no unique relation between surface texture and gloss impression. Nonetheless specific measurement techniques and instruments have been developed and adopted in technical standards. Modern gloss-meters are equipped with several assessment geometries with individual scales. The scale for each measurement angle has a certain range for gloss characterisation, where no efforts have been undertaken so far to eliminate the resulting discontinuities between these scales in the transition regions.

Realistic analytical representations of the textured air/paint interface are difficult to develop and so far not applied to studies of textured surface coatings.

Apart from glossy colour shades, matt-finished colour shades are also often used in colour-imparting surface coatings. Only few different methods of controlling the gloss-level of surface coatings are known so far. It is possible to matting a pigmented surface coating or to cover a glossy pigmented surface coating by a matt clear-coat layer. Adding a matting agent to a paint formulation is most frequently used to introduce the desired degree of surface texture to a polymeric material. These matting agents are homogeneously dispersed in the embedding medium; the effect of matting is achieved by some micro-heterogeneity inside the layer that produces an increase of diffuse light scattering from the sample surface. Different inorganic compounds such as precipitated silica, kaolin, bentonite, or others serve as matting agents.

Current colour development or batch shading processes for matt-finished colour shades make use of two different instrumental approaches depending on whether an integrating sphere instrument or an instrument equipped with a collimated (directional) measurement geometry is utilised.

In case of the integrating sphere instrument with measurement geometries of d/8° (diffuse illumination and measurement at 8°) or 8°/d (illumination at 8° and diffuse measurement), the difference spectrum $\Delta R=R(SPIN)-R(SPEX)$ between specular included (SPIN) and specular excluded (SPEX) readings is a function of surface gloss determined by the matting agent amount. Once this relation has been established by means of an appropriate set of calibration panels, the measured difference spectrum can be adopted to derive the matting agent amount (MAA) needed in a formulation to match a matt-finished colour standard.

In case of instruments equipped with a collimated measurement geometry (as, e.g., 45°/0° (illumination at 45° and measurement at 0°) or other angles) optimum colour recipe predictions can only be expected for colour standards with a gloss level above gloss≈30 units measured at the 60° geometry. In case of dull samples the spectrophotometer will pick up an undefined amount of surface gloss resulting in a suboptimal prediction for the pigmentation. Below this limit the quality of predicted formulas deteriorates considerably with decreasing degree of surface gloss. A gloss measurement instrument (gloss-meter) has to be utilised to establish a calibration function for the matte adjustment amount $(MAA)=f$ (gloss) relation at the three different gloss geometries recommended in technical standards. These two methods of colour recipe calculation for matt colour standards are disclosed in EP 1631802. The methods make reference to colour pigment and colour recipe databases for glossy colour shades which permit matt colour samples to be matched. For both methodic approaches the same set of calibration panels can be utilised to define the $MAA=f(gloss)$ relationship.

The above methods still include a gap concerning the unification of the two approaches for integrating sphere colour measurement instruments and spectrophotometers equipped with a collimated 45°/0° measurement geometry. A further disadvantage is that an additional gloss measurement device is necessary to obtain gloss values.

Accordingly there is still a need for a handy procedure for automating the colour development process. There is in particular a need for a handy and easy procedure for obtaining gloss values for colour standards, e.g. for matt colour standards.

SUMMARY OF THE INVENTION

Methods for determining the gloss of a colour standard are provided. In an exemplary embodiment, a method for determining the gloss of a colour standard includes determining an experimentally determined reflection spectrum R(exp) of a colour standard comprising a first reflection spectrum and a second reflection spectrum. The first reflection spectrum (A1) includes a specular component, and the second reflection spectrum (A2) excludes the specular component. The reflection spectra data of the experimentally determined reflection spectrum R(exp) are converted to a gloss value by acquiring a difference reflection spectrum ΔR with the first reflection spectrum (A1) and with the second reflection spectrum (A2). A gloss value corresponding to the difference reflection spectrum ΔR is determined with the assistance of a previously prepared calibration curve representing a functional relationship between the difference reflection spectrum ΔR and the gloss value measured at one or more gloss angles.

In another embodiment, a method of determining a gloss of a colour standard includes determining an experimentally determined colour position of the colour standard. The experimentally determined colour position includes a specular included colour standard (A1) and a specular excluded colour standard (A2). The experimentally determined colour position is converted to a gloss value by acquiring a difference colour standard with the specular included colour standard (A1) and the specular excluded colour standard (A2), and determining the gloss value with the assistance of a previously prepared calibration curve representing a functional relationship between the difference colour standard and the gloss value measured at one or more gloss angles.

In yet another embodiment, a method for producing a coating composition having one or more matting agents is provided. The method includes determining a gloss value of a colour standard by determining an experimentally determined reflection spectra R(exp) of the colour standard, where the experimentally determined reflection spectra R(exp) includes a first reflection spectrum (A1) with a specular component included and a second reflection spectrum (A2) with the specular component excluded. The reflection spectra data of the experimentally determined reflection spectra R(exp) is converted to a gloss value by acquiring a difference reflection spectrum ΔR with the first reflection spectrum (A1) and with the second reflection spectrum (A2), and determining the gloss value corresponding to the difference reflection spectrum ΔR with the assistance of a previously prepared calibration curve representing a functional relationship between the difference reflection spectrum ΔR and the gloss value measured at one or more gloss angles. A colour recipe is determined for the coating composition based on the colour standard, and the coating composition is produced based on the colour recipe.

BRIEF DESCRIPTION OF THE DRAWINGS

The gloss values have been measured with the micro TRI-gloss instrument of BYK-Gardner. In FIGS. 3A to 3C the reflectance data has been measured with the colour measurement instrument SP64 of X-Rite, in FIGS. 4A to 4C the reflectance data has been measured with the colour measurement instrument SF600 of Datacolor International, and in FIGS. 5A to 5C the reflectance data has been measured with the colour measurement instrument Color-Eye 7000 of Gretag-Macbeth.

DETAILED DESCRIPTION OF THE EMBODIMENTS

Figure 1A:
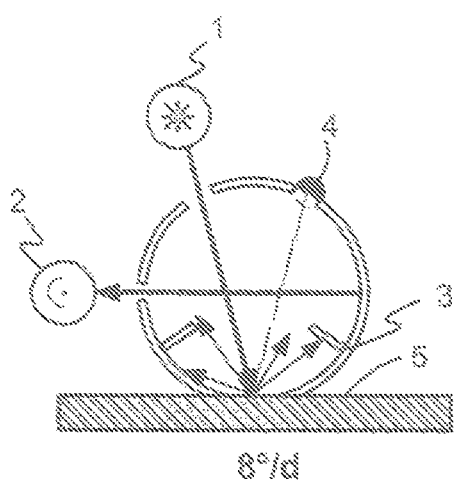
FIGS. 1A and 1B illustrate the standard d/8° and 8°/d measurement geometries, respectively, recommended by technical standards (as, e.g., DIN 5033) to be used for glossy and matt solid colour standards.

These and other features and advantages of the present invention will be more readily understood, by those of ordinary skill in the art, from a reading of the following detailed description. It is to be appreciated that those certain features of the invention, which are, for clarity, described above and below in the context of separate embodiments, may also be provided in combination in a single embodiment. Conversely, various features of the invention that are, for brevity, described in the context of a single embodiment, may also be provided separately or in any sub-combination. In addition, references in the singular may also include the plural (for example, "a" and "an" may refer to one, or one or more) unless the context specifically states otherwise.

"Colour standard" shall mean herein and in the following any coated or coloured surface for which gloss values are to be determined. A colour standard can be a cured or dried paint layer, a wet paint layer, an inherently coloured surface of a substrate or any other coloured substrate of arbitrary character. When measuring the reflectance spectrum of wet paint films typical methods and devices for measuring wet paint films can be used. The colour standard can be, for example, a surface of a substrate to be repair coated or a part thereof, in particular the coated surface of a car body to be repair coated, or a part thereof. The colour standard comprises colour standards with different surface gloss. It includes glossy and matt colour standards, solid colour standards, effect colour standards and combinations thereof.

"Matt colour standard" shall mean herein and in the following any colour standard which does not have a perfectly glossy surface. The matt colour standard also includes so-called semi-glossy colour standards. The initial gloss of a colour standard can be decreased to a desired gloss value, for example, by adding one or more matting agents to the paint composition creating a matt colour standard.

"Solid colour standard" shall mean herein and in the following a colour standard with the optical property of isotropically reflecting a beam of collimated or diffuse incident light. If, e.g., such a colour standard is illuminated by a collimated beam of light at a constant angle, the level of the reflected light and with it the colour will be independent on the viewing angle. Such colour standards can be formulated by means of solid pigments or dyes which may be embedded and dispersed in different media like paint, ceramic, glass, or plastic etc.

"Solid pigment" shall mean here and in the following an inorganic or organic substance consisting of small particles which are practically insoluble in the applied medium and used owing to their colouring, protective, or electromagnetic properties. Solid pigments can be characterised by their chemical composition and their optical and technical properties. Their optical properties are determined by their light scattering and absorbing properties which can be selective (coloured pigments) or a selective (black and white pigments). The solid colour pigments used in the method according to the invention comprise conventional inorganic and/or organic absorption pigments, as are used in coating production. Examples of inorganic or organic colouring pigments are titanium dioxide, iron oxide pigments, carbon black, azo pigments, phthalocyanine pigments, quinacridone, or pyrrolopyrrole pigments.

"Effect pigment" shall mean herein and in the following any platelet-like pigment which, besides colour, imparts to a substrate additional optical properties such as angle-dependent colour, lightness travel, and visual texture. The palette of effect pigments is diverse and can be divided into interference and mirror-like reflective pigments.

"Colorant system" shall mean herein and in the following any system of solid and/or effect pigments, comprising all pigments which shall be used for the production or formulation of paints. The number and choice of pigment components are not subject to restrictions here. They may be adapted in any manner to the relevant requirements, e.g., according to the requirements of the paint manufacturer or its customers.

The term "colour standard" can be used here and in the following interchangeably with the terms "colour sample" and "colour shade". The term "matt solid colour standard" can be used here and in the following interchangeably with the terms "matt solid colour sample" and "matt solid colour shade".

The principle and the individual steps of the method according to the invention are explained in greater detail below.

The method of the present invention is a method for determining the gloss of a colour standard. As defined above the colour standard can be a matt solid colour standard, a matt effect colour standard, a glossy solid colour standard or a glossy effect colour standard. The method is preferably used for determining the gloss of a matt solid colour standard. Therefore, here and in the following the term matt solid colour standard is used. However, it goes without saying that the method of the present invention also includes a method for determining the gloss of a matt effect colour standard, a glossy solid colour standard and a glossy effect colour standard. Thus, the individual steps and features explained in greater detail below are related to a method for determining the gloss of all of the above defined colour standards.

The starting point is a matt solid colour standard for which gloss values are to be determined. This can be, for example, a matt solid colour standard which is to be matched or for the matching of which a suitable colour recipe is to be developed.

First of all, in accordance with step A) of the method according to the invention, the reflection spectra R(exp) of the matt solid colour standard, comprising a first reflection spectrum and a second reflection spectrum, are experimentally determined over a defined wavelength range with the help of an integrating sphere colour measurement instrument, e.g. a spectrophotometer, equipped with a d/8° measurement geometry or a 8°/d measurement geometry. The reflection spectra are preferably determined over a wavelength range of 400-700 nm. The reflection spectra are measured at d/8° geometry with the specular component included (A1) and at d/8° geometry with the specular component excluded (A2). It goes without saying and is well known to a person skilled in the art that an integrating sphere colour measurement instrument can be equipped with a d/8° measurement geometry or alternatively with a 8°/d measurement geometry since both measurement geometries are equivalent measurement geometries. Therefore, if in the following only the term "d/8° measurement geometry" is used the equivalent 8°/d measurement geometry is also meant and can also be used.

Figure 1B:
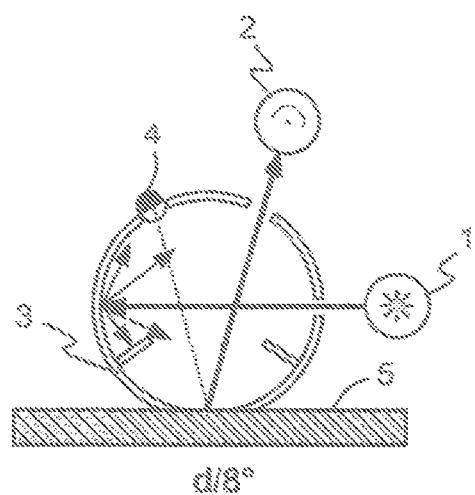

The d/8° measurement geometry can have a light source (1), a detector (2), a baffle (3), a white sphere cap or black trap (4), and is based on diffuse illumination (by means of an Ulbricht sphere) and directional observation at an angle of 8° with respect to the surface normal (d/8°) of a sample (5) (as illustrated in FIGS. 1A and 1B). In the present case of matt solid colour samples, two measurements have to be made operating the instrument in the specular included (A1) and excluded (A2) modes.

D/8° measurement geometries, e.g. according to the one depicted in FIG. 1 are exhaustively described in the specialist literature, are familiar to the person skilled in the art of colour measurement, and are implemented in known conventional measurement instruments. Moreover, the measurement geometries are defined and recommended, e.g., in technical standard DIN 5033 (Farbmessung) or CIE publication 15.3 (colorimetry).

Optionally, e.g., if required for further processing, the colour positions (X, Y, Z, or $L^*$, $a^*$, $b^*$) may be determined or measured in a conventional manner known to the person skilled in the art of colour measurement. The colour positions may be determined on the basis of the experimentally determined reflection spectrum of the matt solid colour standard for both specular included and excluded data sets. The colour positions may also be measured with an appropriate measuring device. The colour positions may then be used in the following process steps instead of or in addition to the reflection data.

In step B) of the method of the present invention the reflection spectra data of the experimentally determined reflection spectra R(exp) of the matt solid colour standard are converted to gloss values by:

B1) acquiring the difference reflection spectrum $\Delta R$ of the experimentally determined reflection spectrum R(exp) with the specular component included (A1) and the experimentally determined reflection spectrum R(exp) with the specular component excluded (A2), and B2) determining the gloss values corresponding to said difference reflection spectrum $\Delta R$ with the assistance of previously prepared calibration curves representing the functional relationship between the difference reflection spectrum $\Delta R$ and the gloss values measured at one or more gloss angles.

The determination of the functional relationship between the difference reflection spectrum $\Delta R$ and surface gloss will be explained below in more detail.

Preparation of Calibration Panels

The colour shades to be used to generate the gloss=$f(\Delta R)$ profiles have to cover the entire range of gloss levels, if well-performing gloss=$f(\Delta R)$ model functions shall be established. It is not the number of samples which is important for the model building, but rather a uniform distribution of gloss levels in the sample set. In order to generate the gloss=$f(\Delta R)$ profiles (calibration curves) a new preparation of a special set of calibration panels may not be needed if history data (gloss data and R(exp) with specular component included and excluded) are already available. If such a sample set of history data is not available, a special set of calibration panels needs to be prepared which later can be augmented by additional history data. Basis for preparing the calibration panels is the available colorant system.

In order to keep the number of calibration panels as low as possible and high enough to achieve the envisaged accuracy and to be representative for the respective paint mixing system and related colour system, panels have to be prepared only for a subset of pigments. Such a subset may comprise black, white, red, green, blue, yellow and violet pigments, where the coloured pigments are blended with the white mixing paint of the paint system, while the neutral pigments are used as masstones. One-layer top coat systems already form glossy surfaces, while in case of two-layer top coat systems (base coat+clear coat) the pigmented base-coat has to be covered by a glossy clear-coat. This set of panels defines the glossy end of the ladder of surface texture. All of these formulas have to be blended with a matting agent (in case of one-layer top coat systems) or covered by a matted clear-coat (in case of two-layer top coat systems) to adjust the desired level of surface gloss. For each paint system generally a natural upper limit for the addition of matting agent to the base-coat or clear-coat exists, which will define the second extreme matt end of the ladder of surface texture. The glossy variant will assume gloss values of the order of 90-100 units, while gloss-values of the other extreme of matt-finished variant will be of the order of less than 5 units. These two extreme points of the ladder of surface texture have to be supplemented by N further calibration panels with gloss values almost equally spaced between the two extreme points. Preparation of, for example, about N=4 to 6 panels per pigment of varying gloss level will be sufficient for the definition of a well-balanced calibration echelon.

In a well-behaved paint system preparation of calibration panels for a single pigment would be sufficient to define a generalized instrument profile. This ideal situation is barely met in practical applications of one-layer top coat paint systems. Integration of pigments into the boundary layer between paint and air will have an impact on the surface gloss and add coloured contributions to the regularly reflected neutral gloss component. Hence, even if the same amount of matting agent is used in different colour formulas the corresponding surface gloss level may vary considerably.

An alternate approach for the definition of generalized instrument profiles can be taken if a sufficiently high number of history data sets of previously developed matt-finished colour shades are available. Plotting surface gloss values versus the difference measure of specular included and excluded reflectance spectra at each gloss assessment geometry will also provide calibration curves if the paint system is well-behaved and a good correlation between both quantities exists.

The calibration curves are generated for a specific pair of instruments: the colour measurement instrument and the gloss measurement instrument.

Gloss Measurement

For the instrumental gloss characterisation collimated measurement geometries have been recommended in technical standards. In case of glossy samples the light partially reflected at the air/paint interface follows the reflection law (angle of reflection=angle of illumination) and can be quantitatively described by Fresnel's equations. The intensity of the reflected light depends on the angle of the incident light and the optical material properties (complex refractive index). The component refracted into the medium undergoes selective absorption and scattering when interacting with the embedded pigment particles and is almost diffusely reflected from the layer. This diffusely reflected light likewise contributes to the specularly reflected component and therefore also has an effect on gloss perception. In case of textured surfaces the light reflected from the surface can be divided into a specular and a diffuse reflected component. With increasing degree of surface roughness the energy of the specularly reflected component will steadily decrease and progressively contribute to the diffusely reflected component.

Figure 2:
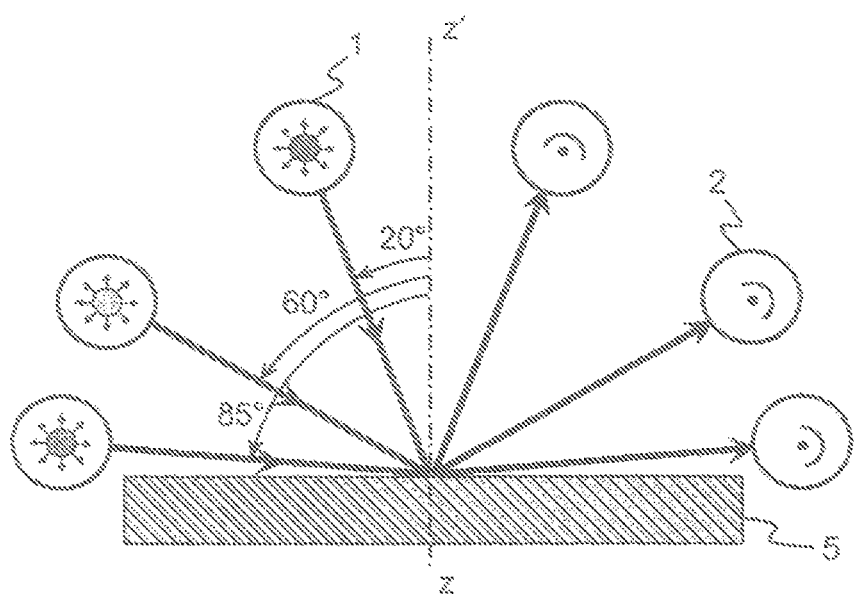
FIG. 2 displays the recommended geometrical conditions for the measurement of surface gloss.

Surface gloss is experimentally determined by means of an appropriate gloss measurement instrument, i.e. a reflectometer according to technical standards DIN 67530 or ASTM D 523-89, defining the experimental conditions to instrumentally assess surface gloss. A reflectometer typically contains a light source (1) and a detector (2) over the sample (5) (see FIG. 2). Within the technical standard three different measurement geometries are recommended to characterise the surface gloss at about 20°, about 60°, and about 85° with respect to the surface normal (z-z') (see FIG. 2) The 20° angle is used to characterise glossy samples, the 60° angle is recommended for semi-glossy samples, and the 85° angle is supposed to provide reliable information for matt samples.

The measured reflectometer values are referred to the corresponding values of a glossy black glass having a refractive index of n=1.567. The black glass has an assigned specular gloss value of 100 for each measurement geometry. Since none of the recommended measurement angles will provide results of highest accuracy for all gloss levels (see FIG. 2) the first step in determining the gloss level of a specimen is to identify the appropriate measurement geometry. If the 60° gloss value is between about 10 and about 70 units, this is supposed to be the correct measurement geometry. If the 60° gloss is lower than about 10 units, the 85° geometry should be used instead, while the 20° geometry result will be advantageous for comparison in case the 60° value exceeds the 70 units boundary. Consequently, there are two discontinuities in the gloss scale which can only be defused by some kind of averaging of the gloss values obtained at the three measurement geometries.

Figure 7:
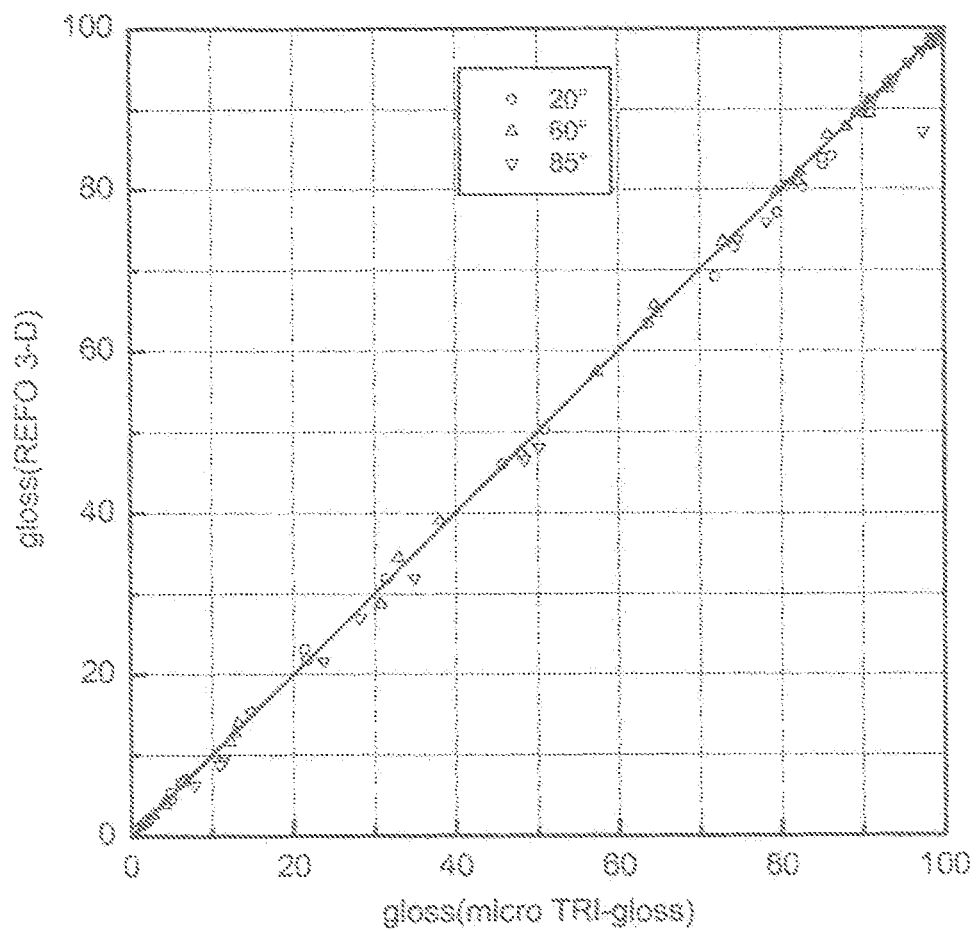
FIG. 7 illustrates the correlation of gloss data obtained by means of two instruments of different manufacturers (micro TRI-gloss of BYK-Gardner and REFO 3-D of Hach Lange GmbH) at all three assessment geometries. The correlation index $r_c$ at all assessment geometries exceeds a value of 0.999 indicating that the instrument scales of both instruments are congruent.

Gloss data obtained by different instruments of different manufacturers are generally commensurable within the experimental errors if their design follows the guidelines recommended in the above-mentioned technical standards. In order to demonstrate the validity of this assertion a set of matt-finished panels of varying degree of surface texture has been measured on two different gloss-meters of different manufacturers (micro TRI-gloss of BYK-Gardner, REFO 3-D of Hach Lange GmbH) for a quantitative comparison. All experimental data obtained are collected in FIG. 7. As can be seen from FIG. 7, all gloss data experimentally determined for both types of gloss-meters are highly correlated with a correlation index of $r_c$>0.999 at all three assessment angles. Within the experimental errors at least these two instrument types can be exchanged without expecting a break in gloss scales which are congruent. Therefore, only gloss data of the micro TRI-gloss instrument of BYK-Gardner have been adopted for all numerical analyses.

Generalised Doss Profiles

Figure 3A:
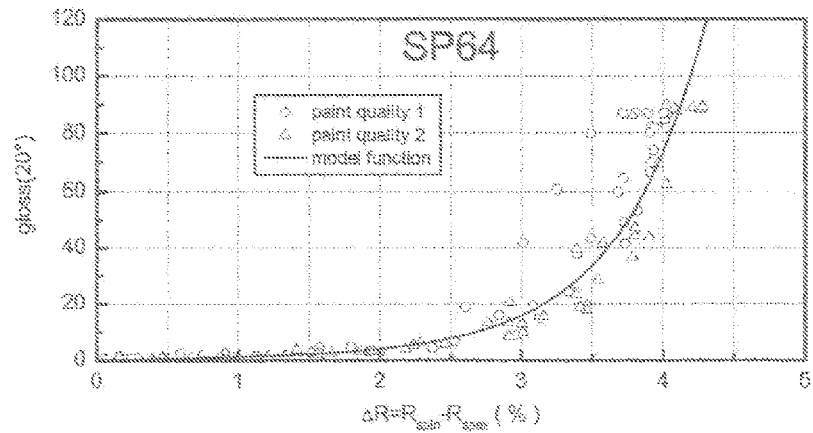
FIGS. 3A to 3C, FIGS. 4A to 4C, and FIGS. 5A to 5C show gloss profiles obtained for three typical integrating sphere colour measurement instruments for the three angle geometries (20°, 60°, and 85°) recommended by technical standards to access surface gloss of matt-finished surface coatings. The continuous curves through the data points represent fits to appropriate model functions. The experimental data sets have been obtained for two different paint systems (paint quality 1 and paint quality 2). Both paint systems represent solvent-based Refinish mixing systems, where paint quality 1 is a balanced quality and paint quality 2 a concentrated quality (pastes). In the latter case formulas have to be completed by the addition of an appropriate amount of binder.
Figure 3B:
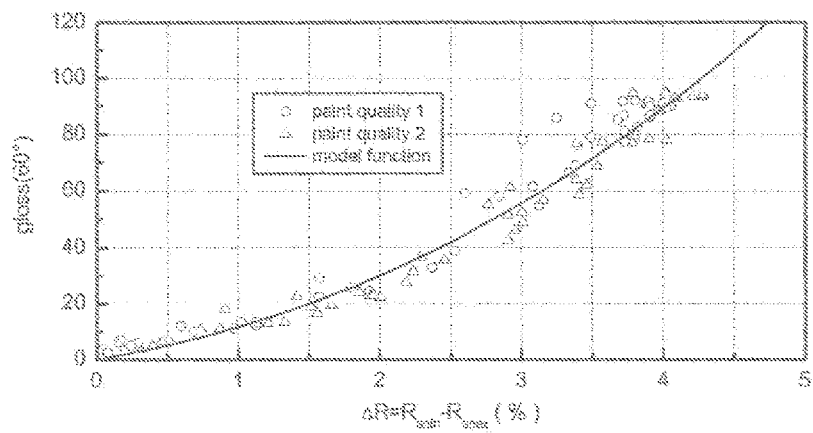
Figure 3C:
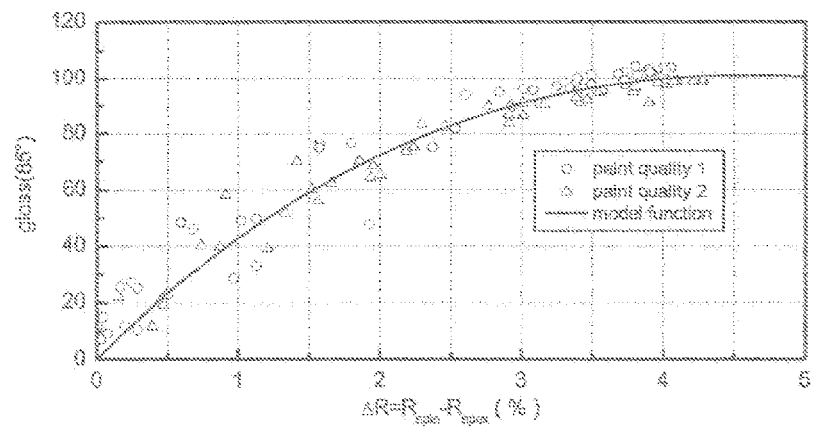
Figure 4A:
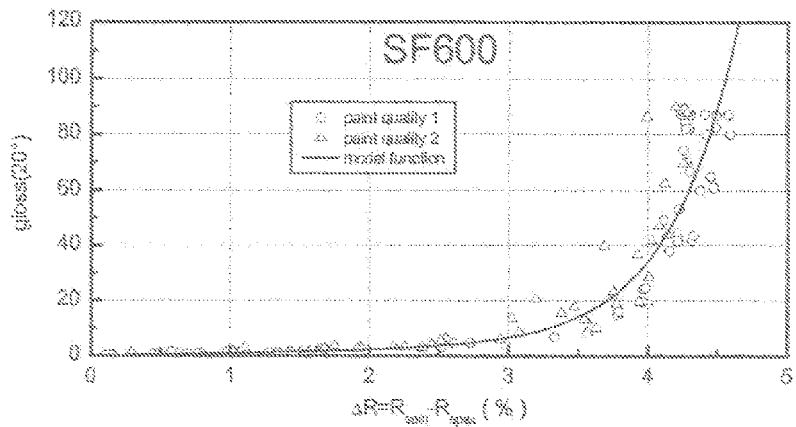
Figure 4B:
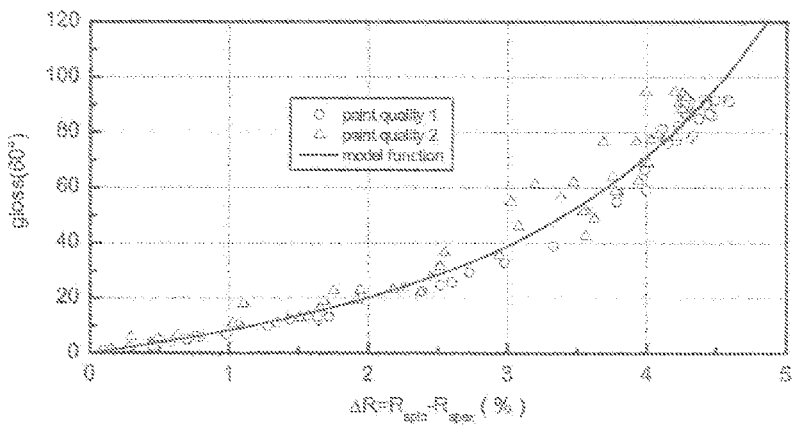
Figure 4C:
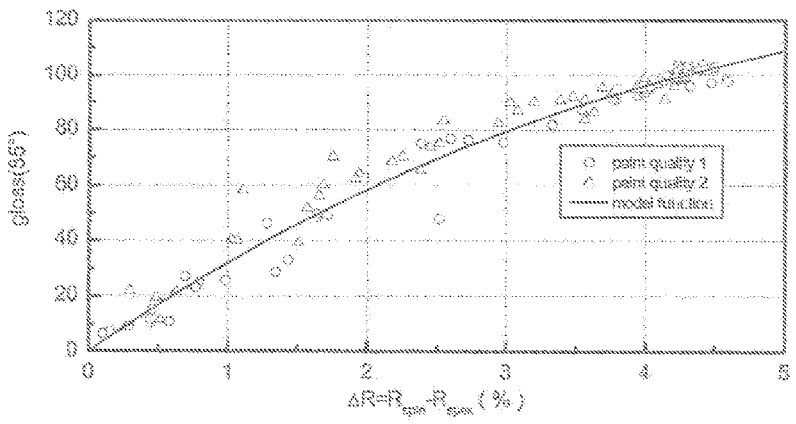
Figure 5A:
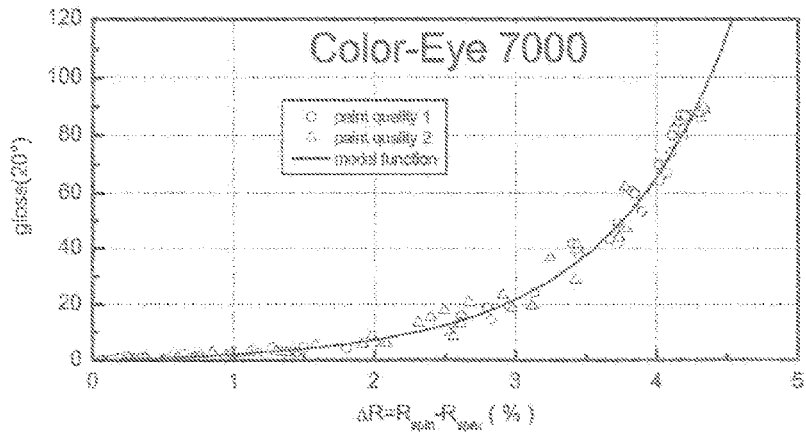
Figure 5B:
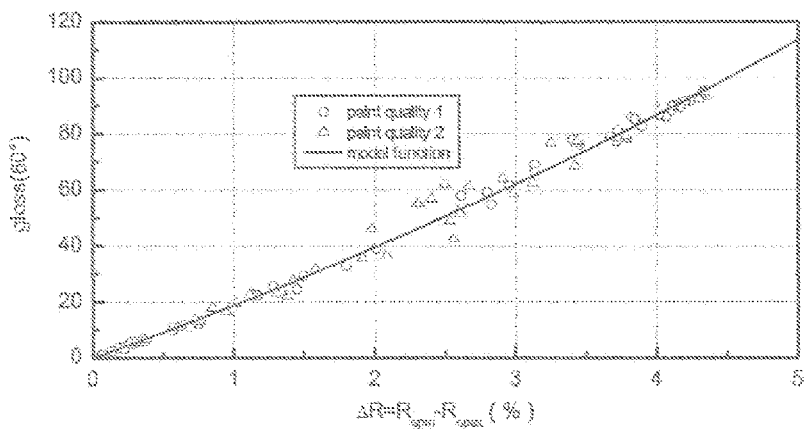
Figure 5C:
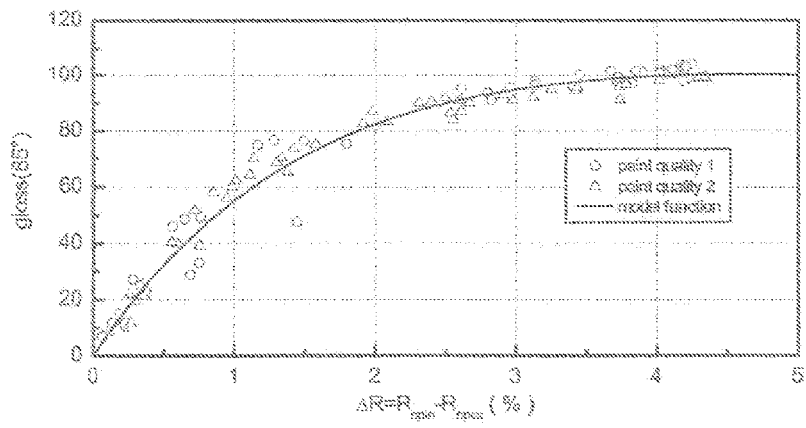

Both gloss and colour readings can be combined in three mathematical models relating gloss data obtained at the three recommended different gloss geometries (20°, 60°, and 85°) to the spectral difference $\Delta R=R(SPIN)-R(SPEX)$ determined by means of an integrating sphere colour measurement instrument. FIGS. 3 to 5 display experimental data for three different colour measurement instruments obtained for carefully chosen sets of calibration panels of two different refinish paint mixing systems along with model functions fitted to the experimental data. Obviously all sets of data are well-behaved and follow universal functions at all three measurement geometries. The functional behaviour can be approximated by a single non-linear model function having only three parameters which have to be adjusted at each gloss angle geometry in the sense of the $L_2$-norm by means of an efficient non-linear fitting routine minimising the sum of weighted squares of residuals between model function and experimental data. The parameter sets depend on the spectrophotometer type utilised for the collection of spectral data. This dependence is a consequence of the fact that each instrument manufacturer uses its own integrating sphere with design parameters chosen for optimum performance of the respective instrument. Size of the sample port and gloss trap, efficiency of the gloss trap, as well as apertures of the optical system will have an impact on the measurement results. The derived gloss profiles can be used to compute gloss values for all three gloss angles for a given difference reflection spectrum $\Delta R$ of the experimentally determined reflection spectrum R(exp) with the specular component included (A1) and the experimentally determined reflection spectrum R(exp) with the specular component excluded (A2).

The performance of the approach of generalized instrument profiles is illustrated below using the example of different types of spectrophotometers of three instrument manufacturers: SP64 of X-Rite, Color-Eye 7000 of Gretag-Macbeth, and SF600 of Datacolor International. All of these instruments are equipped with integrating Ulbricht spheres which can be operated in specular included and specular excluded modes. However, the geometrical size and design of apertures is different for each of these Ulbricht spheres so that for colour standards of varying gloss level different experimental results for the difference R=R(SPIN)–R(SPEX) have to be expected.

In order to define generalized instrument profiles two sets of matt-finished calibration panels of varying gloss levels of two different paint systems have been prepared and measured on all three instruments. Both paint systems represent solvent-based Refinish mixing systems, where paint quality 1 is a balanced quality and paint quality 2 a concentrated quality (pastes). The surface gloss of the entire set of calibration panels has been characterized by means of a micro TRI-gloss instrument of BYK-Gardner (see FIGS. 3-5).

General instrument profiles have been established between an integrating sphere colour measurement instrument and a gloss measurement instrument relating the difference spectrum $\Delta R$=R(SPIN)–R(SPEX) to the gloss values derived at the three recommended gloss-geometries. Therefore, preferably three instrument profiles have to be created. Based on readings taken on an appropriately chosen set of, e.g., matt-finished calibration panels of variable level of surface gloss and independent gloss measurements, calibration curves (profiles) can be generated relating the difference spectrum $\Delta R$=R(SPIN)–R(SPEX) to the gloss values obtained at the three standard measurement geometries. These calibration curves are independent of the paint quality chosen (if the paint quality is well-behaved and will not integrate pigment particles into the air/paint interface) and only depend on the optical details and configuration of the hardware used (spectrophotometer, gloss-meter). For each pair of instruments—colour measurement instrument and gloss measurement instrument—individual instrument profiles have to be generated.

The gloss values obtained in step B2) can subsequently be used in different ways. The gloss values can be directly used, e.g. to compare gloss values of different colour standards. They can also be used in subsequent processes, for example, they can be fed into a gloss profile converter relating surface gloss and matting agent amount, to derive the matting agent amount needed to match a matt solid colour standard.

The quantity of matting agent corresponding to the determined degree of gloss of a matt solid colour standard can be determined with the assistance of previously prepared calibration curves for an available colorant system. The calibration curves were prepared by previously measuring the degree of gloss at one or more gloss angles on calibration panel sets containing differing quantities of matting agents and plotting the degree of gloss as a function of matting agent concentration.

The determined quantity of matting agent may then be output separately or the determined quantity of matting agent is directly suitably incorporated into a previously determined colour recipe. In the latter case the quantity of matting agent is combined with the colour recipe obtained, so obtaining a colour recipe to match the matt solid colour standard, whose recipe contains the nature of the colour-imparting pigments and the concentrations thereof and in addition the quantity of matting agent.

Thus, the method of the present invention can be combined with or used in the course of a standard recipe calculation and shading process.

For example, a recipe for a colour standard based on experimentally determined reflection spectra R(exp) can be calculated by usual recipe calculation methods, wherein the experimentally determined reflection spectrum R(exp) with the specular component included, which has been corrected for the specular component, is matched by using the optical material parameters of the pigments of an available colorant system for the preparation of colour shades, so obtaining a colour recipe specifying the nature of the pigments and the concentration thereof. Alternatively, the experimentally determined reflection spectrum R(exp) with the specular component included, which has been corrected for the specular component can be compared with the reflection spectra associated to colour recipes of a colour recipe database for colour shades and identifying from said colour recipe database the reflection spectrum which comes closest to the experimentally determined reflection spectrum R(exp) of the colour standard and the associated colour recipe can be identified. These processes proceed in accordance with the art using pigment databases, e.g. discrete solid pigment (colouring pigment) databases or colour recipe databases containing the required optical material parameters of the pigments of the available colorant system. In case of matt solid colour shades it is advantageous that it is possible to access colorant systems or colour recipes as are used for producing glossy colour shades. Such processes are described, for example, in EP 1 631 802. Useful matting agents comprise conventional products, which are familiar to the person skilled in the art of colour development and are generally commercially available. The matting agent may be inorganic or organic in nature. Examples of inorganic matting agents are amorphous or pyrogenic silica, silica gels and phyllo-silicates, for example, hydrated magnesium silicate (talcum). The inorganic matting agents may be present in untreated form or in a form surface-treated with organic compounds, for example, with suitable grades of wax, or also with inorganic compounds. Examples of organic matting agents are Al, Zn, Ca or Mg stearate, waxy compounds, such as for example micronized polypropylene waxes, together with urea/formaldehyde condensation products.

Figure 6:
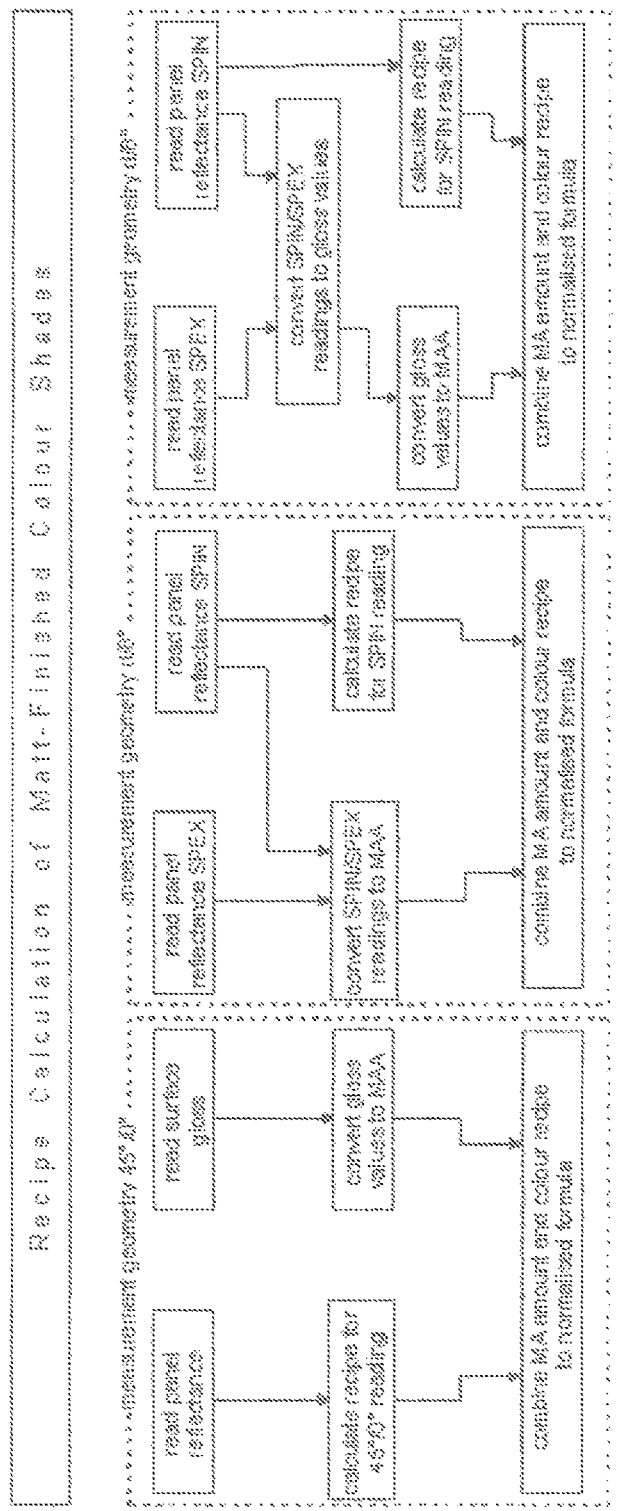
FIG. 6 shows the process flow chart of a recipe calculation procedure of matt-finished colour shades for the two standard measurement geometries 45°/0° (left part of diagram; MAA=matting agent amount) and d/8° (middle part of diagram). The right part of the diagram displays the new process flow when converting spectral data to gloss values, before converting these gloss values to a matting agent amount.

The process flow for the known approaches to recipe calculation of matt-finished colour shades and the new approach of the present invention is depicted in FIG. 6, i.e. the known process with measurement geometry 45°/0° with gloss measurement; the known process with measurement geometry d/8° without gloss measurement and without obtaining gloss values; and the method according to the invention with measurement geometry d/8° and without gloss measurement, but with obtaining gloss values.

It goes without saying that all data used in the method of the invention, for example, the previously prepared calibration curves are preferably stored in a database.

The method of the present invention can advantageously be used in all areas of application, where gloss values of colour standards, e.g. matt colour standards, in particular matt solid colour standards, have to be determined. This may include, for example, applications where matt colour standards, in particular matt solid colour standards, have to be developed, for example, in automotive and industrial coatings applications. In automotive coatings the method can be used for OEM coatings as well as refinish coatings as, e.g., in colour laboratories, in refinish body shops, in the paint manufacturing process, and in standardisation of paints. The method is applicable to matt and glossy colour standards of known or unknown pigmentation.

The main advantage of the method of the present invention is that an integrating sphere spectrophotometer (d/8°—spectrophotometer) is capable of generating gloss information for the three standard measurement geometries of typical gloss measurement devices (20°, 60°, and 85°; see FIG. 3), in addition to the spectral information. Therefore, the functionality of the integrating sphere spectrophotometer is extended considerably, since now in a practical application, for example, in the colour tools used in refinish body-shops, the integrating sphere spectrophotometer can replace the glossmeter, which is needed in this type of application when utilising spectrophotometers equipped with a collimated 45°/0° measurement geometry.

In addition MAA=f(gloss) gloss profiles can be determined based on the so obtained gloss information. The MAA=f (gloss) gloss profiles can be used for both types of colour measurement instruments, colour measurement instruments with d/8° geometry and colour measurement instruments with 45°/0° geometry. Generally the method of the present invention can be used in any application where determination of reflectance data and gloss data is desired, e.g. in the evaluation of weathering tests. Processing times can thus be reduced.

This invention is also directed to a process for producing a coating composition having one or more matting agents. The process can comprise the steps of:

i) providing a colour standard having a gloss value determined by any of the methods disclosed herein;

ii) determining a colour recipe for the coating composition based on the colour standard; and iii) producing the coating composition based on the colour recipe.

Particularly, the colour recipe can comprise data for the amount of one or more matting agents that are required for producing the coating composition having a desired gloss value.

The colour standard can be a matt solid colour standard. The coating composition can be an OEM automotive coating composition, a refinish coating composition, or a combination thereof. This disclosure is further directed to a coating composition produced according to the process disclosed above.

The following Examples illustrate the invention in greater detail:

EXAMPLES

Two semi-glossy colour shades from the RAL 840-HR register (RAL 3000, RAL 7005), representing a well-accepted and typical collection of colour standards in industrial applications, have been selected to show the efficiency of the method of the present invention. The reflectance functions of the two selected colour standards have been experimentally determined within the visible spectral range. The commercial measurement instrument used for the colour development was equipped with a d/8° measurement geometry and could be operated in the specular included (SPIN) and excluded (SPEX) modes. This was the same colour measurement instrument as used to determine the calibration function. The gloss values have been measured at the three recommended angles of 20°, 60°, and 85° using the same commercial glossmeter that had been used to determine the calibration function. The calibration curve of the pair of instruments used (gloss-meter=micro TRI-gloss instrument of BYK-Gardner; colour measurement instrument=SP64 of X-Rite) is shown in FIG. 3 (FIGS. 3A-3C).

Both colour standards have been processed through the standard procedure of colour development using a set of optical material parameters (wavelength-dependent scattering and absorption coefficients) derived from a set of glossy calibration panels. After identifying the appropriate pigmentation of the optimised recipe the formulation is sprayed out, re-measured and corrected in further steps (if necessary) using an efficient recipe correction algorithm.

Table I shows the experimental results (colour and gloss information) of the two test colour standards (RAL 3000 and RAL 7005). The colour standards have been worked out in a solvent-based refinish paint line for passenger cars (Standox 2K-acrylic). In the three columns specifying the surface gloss the gloss numbers in bold (second row, respectively) are derived from the generalised instrument profile, while those depicted in normal mode (first row, respectively) have been determined experimentally by means of a gloss measurement instrument. (STD—standard; R—recipe; CR—corrected recipe).

As can be deferred from Table I the level of surface gloss could be adjusted quite precisely using the outlined calibration function, at least within the limitations set by the standard deviation obtained for the model functions (see Tab. II).

Table II shows the standard deviation (STDDEV) obtained for the model functions when matched to the experimental data at all three gloss assessment geometries for three different spectrophotometers. This statistical measure estimates the achievable accuracy of the respective general instrument profile. As can be seen from Tab. II the performance of the Color-Eye 7000 instrument profile is significantly better than those obtained for the other two spectrophotometers at the 20° and 60° assessment geometries and slightly better at the 85° gloss geometry. The performance of the SP64 and SF600 instruments is very similar, where the standard deviation at the 20° gloss geometry is about twice as large compared to the 60° and 85° gloss geometries. In view of the experimental variance of the measured data the chosen type of model function describes the data set to a sufficient degree of accuracy and can be adopted to convert the measured R difference spectra to gloss values.

TABLE I

|  |  | L*<br>L* | a*<br>a* | b*<br>b* | C*<br>C* | $h_{ab}$<br>H* | E*(76) | E*(94) | Gloss<br>(20°) | Gloss<br>(60°) | Gloss<br>(85°) |
|---|---|---|---|---|---|---|---|---|---|---|---|
| RAL<br>3000 | STD | 35.0 | 52.30 | 41.70 | 66.90 | 38.60 | — | — | 13.2<br>12.8 | 58.9<br>50.5 | 88.5<br>87.4 |
|  | 1R | −0.07 | 0.51 | 0.73 | 0.85 | 0.25 | 0.89 | 0.26 | 25.1<br>3.1 | 34.6<br>25.7 | 78.9<br>66.8 |
|  | 1CR | −0.14 | 0.22 | 0.68 | 0.60 | 0.39 | 0.73 | 0.29 | 36.8<br>15.5 | 77.1<br>53.9 | 95.3<br>89.3 |
| RAL<br>7005 | STD | 44.9 | −1.70 | 2.90 | 3.40 | 120.70 | — | — | 2.1<br>2.5 | 18.7<br>22.5 | 36.2<br>62.6 |
|  | 1R | 1.72 | 0.45 | 1.45 | 1.16 | −0.98 | 2.29 | 2.29 | 1.7<br>1.3 | 15.6<br>14.2 | 50.9<br>47.6 |
|  | 1CR | −1.25 | 0.11 | −0.16 | −0.19 | −0.01 | 1.27 | 1.26 | 1.9<br>1.5 | 17.4<br>15.8 | 55.0<br>51.0 |
|  | 2CR | 0.47 | 0.04 | −0.10 | −0.10 | 0.01 | 0.48 | 0.48 | 3.2<br>3.2 | 24.9<br>26.1 | 58.6<br>67.4 |

TABLE II

| | STDDEV | | |
|---|---|---|---|
| Instrument | 20° | 60° | 85° |
| SP64 | 12.19 | 6.46 | 7.15 |
| SF600 | 14.10 | 6.51 | 5.82 |
| Color-Eye 7000 | 3.60 | 2.99 | 5.00 |

What we claim is:

1. A method for determining a gloss of a colour standard, said method comprising the steps of:
   A) experimentally determining a reflection spectrum R(exp) of the colour standard, comprising a first reflection spectrum and a second reflection spectrum, with an integrating sphere colour measurement instrument, wherein said first reflection spectrum is obtained at
      (A1) d/8°—geometry or 8°/d—geometry with a specular component included; and
   said second reflection spectrum is obtained at
      (A2) d/8°—geometry or 8°/d—geometry with the specular component excluded; and
   B) converting reflection spectra data of the experimentally determined reflection spectrum R(exp) of the colour standard to a gloss value by:
      B1) acquiring a difference reflection spectrum ΔR of the experimentally determined reflection spectrum R(exp) with the specular component included (A1) and the experimentally determined reflection spectrum R(exp) with the specular component excluded (A2); and
      B2) determining the gloss value corresponding to said difference reflection spectrum ΔR with the assistance of a previously prepared calibration curve representing a functional relationship between the difference reflection spectrum ΔR and the gloss value measured at one or more gloss angles.

2. The method of claim 1, wherein said colour standard is a matt solid colour standard.

3. The method according to claim 1, wherein an X, Y, and Z colour position, or an L*, a*, and b* colour position, are derived from the reflection spectrum R(exp), and wherein the X, Y, and Z colour position or the L*, a*, and b* colour position is used in addition to the reflection spectra to determine the gloss value.

4. The method according to claim 1, wherein an X, Y and Z colour position, or an L*, a*, and b* colour position are measured, and wherein the X, Y, and Z colour position or the L*, a*, and b* colour position is used in addition to the reflection spectra to determine the gloss value.

5. The method according to claim 1, wherein the reflection spectrum R(exp) is measured with a spectrophotometer with the d/8°—geometry or with the 8°/d—geometry.

6. The method according to claim 1, wherein the reflection spectrum R(exp) is acquired over a wavelength range of from about 400 nanometers (nm) to about 700 nm.

7. The method according to claim 1 further comprising:
   standardizing paint using the gloss value.

8. The method according to claim 1 further comprising:
   using the gloss value in an original equipment manufacturer automotive coating.

9. The method according to claim 1 further comprising:
   using the gloss value in a refinish coating.

10. A method for determining a gloss of a colour standard, said method comprising the steps of:
    A) experimentally determining a colour position of the colour standard, wherein said colour position comprises:
       (A1) a specular included colour standard; and
       (A2) a specular excluded colour standard; and
    B) converting the experimentally determined colour position of the colour standard to a gloss value by:
       B1) acquiring a difference colour standard of the experimentally determined colour position with the specular included colour standard (A1) and the specular excluded colour standard (A2); and
       B2) determining the gloss value corresponding to said difference colour standard with the assistance of a previously prepared calibration curve representing a functional relationship between the difference colour standard and the gloss value measured at one or more gloss angles.

11. The method of claim 10 wherein experimentally determining the colour position of the colour standard comprises experimentally determining an X, Y, and Z colour position of the colour standard.

12. The method of claim 10 wherein experimentally determining the colour position of the colour standard comprises experimentally determining an L*, a*, and b* colour position of the colour standard.

13. A method for producing a coating composition having one or more matting agents, said method comprising the steps of:
    i) determining a gloss value of a colour standard by:
       A) experimentally determining a reflection spectrum R(exp) of the colour standard, comprising a first reflection spectrum and a second reflection spectrum, with an integrating sphere colour measurement instrument, wherein said first reflection spectrum is obtained at (A1) d/8°—geometry or 8°/d—geometry with a specular component included; and said second reflection spectrum is obtained at (A2) d/8°—geometry or 8°/d—geometry with the specular component excluded; and B) converting reflection spectra data of the reflection spectrum R(exp) of the colour standard to the gloss value by:

B1) acquiring a difference reflection spectrum ΔR of the reflection spectrum R(exp) with the specular component included (A1) and the reflection spectrum R(exp) with the specular component excluded (A2); and B2) determining the gloss value corresponding to said difference reflection spectrum ΔR with the assistance of a previously prepared calibration curve representing a functional relationship between the difference reflection spectrum ΔR and the gloss value measured at one or more gloss angles;

ii) determining a colour recipe for said coating composition based on said colour standard; and iii) producing said coating composition based on said colour recipe.

14. The method of claim 13, wherein said colour standard is a matt solid colour standard.

15. The method of claim 13, wherein said coating composition is an original equipment manufacturer automotive coating composition, a refinish coating composition, or a combination thereof.

* * * * *